US011690896B2

(12) United States Patent
Koob et al.

(10) Patent No.: US 11,690,896 B2
(45) Date of Patent: *Jul. 4, 2023

(54) NON-SURGICAL, LOCALIZED DELIVERY OF COMPOSITIONS FOR PLACENTAL GROWTH FACTORS

(71) Applicant: MiMedx Group, Inc., Marietta, GA (US)

(72) Inventors: Thomas J. Koob, Marietta, GA (US); Rebeccah J. C. Brown, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 799 days.

This patent is subject to a terminal disclaimer.

(21) Appl. No.: 16/709,064

(22) Filed: Dec. 10, 2019

(65) Prior Publication Data

US 2020/0113973 A1    Apr. 16, 2020

Related U.S. Application Data

(63) Continuation of application No. 15/797,335, filed on Oct. 30, 2017, now Pat. No. 10,517,931, which is a continuation of application No. 14/845,199, filed on Sep. 3, 2015, now Pat. No. 9,827,293, which is a continuation-in-part of application No. 14/157,444, filed on Jan. 16, 2014, now Pat. No. 9,655,948.

(60) Provisional application No. 61/956,185, filed on Jan. 17, 2013.

(51) Int. Cl.
| | | |
|---|---|---|
| *A61K 38/18* | (2006.01) | |
| *A61K 9/16* | (2006.01) | |
| *A61K 35/50* | (2015.01) | |
| *A61K 9/00* | (2006.01) | |
| *A61K 47/10* | (2017.01) | |
| *A61L 15/32* | (2006.01) | |
| *A61L 15/40* | (2006.01) | |
| *A61L 15/64* | (2006.01) | |
| *A61L 15/44* | (2006.01) | |

(52) U.S. Cl.
CPC ........ *A61K 38/1866* (2013.01); *A61K 9/0024* (2013.01); *A61K 9/16* (2013.01); *A61K 35/50* (2013.01); *A61K 38/1891* (2013.01); *A61K 47/10* (2013.01); *A61L 15/32* (2013.01); *A61L 15/40* (2013.01); *A61L 15/44* (2013.01); *A61L 15/64* (2013.01)

(58) Field of Classification Search
None
See application file for complete search history.

(56) References Cited

U.S. PATENT DOCUMENTS

| | | |
|---|---|---|
| 2,694,914 A | 11/1954 | Glover, Jr. |
| 4,564,368 A | 1/1986 | Sawyer et al. |
| 4,745,771 A | 5/1988 | Linner et al. |
| 4,968,325 A | 11/1990 | Black et al. |
| 5,118,867 A | 6/1992 | Bahrmann et al. |
| 5,284,655 A | 2/1994 | Bogdansky et al. |
| 6,030,635 A | 2/2000 | Gertzman et al. |
| 6,503,244 B2 | 1/2003 | Hayman |
| 7,311,904 B2 | 12/2007 | Hariri |
| 7,311,905 B2 | 12/2007 | Hariri |
| 8,067,044 B2 | 11/2011 | Henry et al. |
| 8,153,162 B2 | 4/2012 | Tseng et al. |
| 8,323,701 B2 | 12/2012 | Daniel et al. |
| 8,357,403 B2 | 1/2013 | Daniel et al. |
| 8,372,437 B2 | 2/2013 | Daniel |
| 8,372,439 B2 | 2/2013 | Daniel et al. |
| 8,904,664 B2 | 12/2014 | Pringle et al. |
| 2002/0123141 A1 | 9/2002 | Hariri |
| 2002/0160510 A1 | 10/2002 | Hariri |
| 2003/0032179 A1 | 2/2003 | Hariri |
| 2003/0187515 A1 | 10/2003 | Hariri et al. |
| 2004/0048796 A1 | 3/2004 | Hariri et al. |
| 2006/0140913 A1 | 6/2006 | Bhatia |
| 2006/0154860 A1 | 7/2006 | Ceradini et al. |
| 2006/0210532 A1 | 9/2006 | Carmeliet et al. |
| 2006/0233850 A1 | 10/2006 | Michal |
| 2007/0021704 A1 | 1/2007 | Hariri et al. |
| 2007/0021762 A1 | 1/2007 | Liu et al. |
| 2007/0071740 A1 | 3/2007 | Tseng et al. |
| 2007/0202189 A1 | 8/2007 | Ahlfors |
| 2007/0248575 A1 | 10/2007 | Connor et al. |
| 2007/0299043 A1 | 12/2007 | Hunter et al. |
| 2008/0050347 A1 | 2/2008 | Ichim |
| 2008/0069895 A1 | 3/2008 | Liu et al. |
| 2008/0131966 A1 | 6/2008 | Hariri |
| 2008/0181967 A1 | 7/2008 | Liu et al. |

(Continued)

FOREIGN PATENT DOCUMENTS

| | | |
|---|---|---|
| CN | 101433556 | 5/2009 |
| EP | 0 431 479 A1 | 6/1991 |

(Continued)

OTHER PUBLICATIONS

U.S. Appl. No. 15/797,335, filed Oct. 30, 2017, U.S. Pat. No. 10,517,931, Issued.
U.S. Appl. No. 14/845,199, filed Sep. 3, 2015, U.S. Pat. No. 9,827,293, Issued.
U.S. Appl. No. 14/157,444, filed Jan. 16, 2014, U.S. Pat. No. 9,655,948, Issued.
"MiMedx Group Announces Launch of EpiFixTM and Hiring of Vice President, Wound Care," Mimedx Press Release (2011).

(Continued)

*Primary Examiner* — Daniel C Gamett
(74) *Attorney, Agent, or Firm* — Alston & Bird LLP

(57) ABSTRACT

Described herewith are compositions comprising placental growth factors and methods for non-surgical, localized delivery thereof. The composition is delivered to a diseased or injured organ and/or body part and is formulated in a manner which allows for localized retention of the composition at the site of delivery.

10 Claims, No Drawings

(56) References Cited

U.S. PATENT DOCUMENTS

| | | |
|---|---|---|
| 2008/0233552 A1 | 9/2008 | Ma et al. |
| 2009/0012629 A1 | 1/2009 | Yao et al. |
| 2009/0142831 A1 | 6/2009 | Hariri |
| 2009/0291891 A1 | 11/2009 | Neufeld |
| 2010/0028849 A1 | 2/2010 | Shelby et al. |
| 2010/0104539 A1 | 4/2010 | Daniel et al. |
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1 | 8/2010 | Stephen A. et al. |
| 2010/0260847 A1 | 10/2010 | Hariri |
| 2010/0272679 A1 | 10/2010 | Penn et al. |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2013/0095060 A1 | 4/2013 | Hsieh et al. |
| 2013/0218274 A1 | 8/2013 | Spencer et al. |
| 2013/0230561 A1 | 9/2013 | Daniel et al. |
| 2013/0344162 A1 | 12/2013 | Morse et al. |
| 2014/0017280 A1 | 1/2014 | Daniel et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0067058 A1 | 3/2014 | Koob et al. |
| 2014/0106447 A1 | 4/2014 | Brown et al. |
| 2014/0140964 A1 | 5/2014 | Brown et al. |
| 2014/0271728 A1 | 9/2014 | Koob et al. |
| 2014/0369957 A1 | 12/2014 | Bartorelli et al. |

FOREIGN PATENT DOCUMENTS

| | | |
|---|---|---|
| KR | 10/1991/0011727 A | 8/1991 |
| KR | 10199111272 | 8/1991 |
| KR | 0110588 | 11/2001 |
| WO | WO-90/12584 | 11/1990 |
| WO | WO-01/08716 A1 | 2/2001 |
| WO | WO-2005/017165 | 2/2005 |
| WO | WO-2009/033160 A1 | 3/2009 |
| WO | WO-2009/048908 | 4/2009 |
| WO | WO-2009/132186 A1 | 10/2009 |
| WO | WO-2010/029344 A2 | 3/2010 |
| WO | WO-2012/112410 A2 | 8/2012 |
| WO | WO-2012/112417 A2 | 8/2012 |
| WO | WO-2012/112441 A1 | 8/2012 |
| WO | WO-2015/031681 A1 | 3/2015 |
| WO | WO-2015/038477 A1 | 3/2015 |
| WO | WO-2015/109329 A1 | 7/2015 |
| WO | WO-2016/040385 A1 | 3/2016 |
| WO | WO-2016/128916 A1 | 8/2016 |

OTHER PUBLICATIONS

Ahmed et al., Regulation of Placental Vascular Endothelial Growth Factor (VEG F) and Placenta Growth Factor (PlGF) and Soluble Flt-1 by Oxygen—A RevieW, Placenta (2000), 21(14A):516-524.
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
Coulomb-L'Hermine et al., "Letter to the Editor. SDF-1 Production by Placental Cells: A Potential Mechanism of Inhibition of Mother-to-Fetus HIV Transmission", AIDS Research and Human Retroviruses (2000), 16(11): 1097-1098.
EpiFix Product Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
Inokuma et al., "CTACK/CCL27 Accelerates Skin Regeneration via Accumulation of Bone Marrow-Derived Keratinocytes," Stem Cells, 2006, 24:2810-2816.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Koob et al., "Biological properties of dehydrated human amnion/chorion composite graft: implications for chronic wound healing," International Wound Journal, (2013), 10(5):493-500.
Mayfield et al., "Watertight closure of spinal dura mater: Technical note," J. Neurosurg., (1975), 43(5):639-640.
MyBioSource/www.mybiosource.com/prods/Recombinant-Protein/CCL27-CTACK/datasheet.php?products-id-444088 (Accessed Jun. 9, 2015).
Nibbs et al., CCL27/Pesky: A Novel Paradigm for Chemokine Function, 2003, Expert Opin. Biol. Ther., 3(1):15-22.
O'Keefe et al., Keratinocyte Growth-Promoting Activity From Human Placenta, Journal of Cellular Physiology. vol. 124, No. 3, Sep. 1985, pp. 439-445, 7 pages.
PCT International Preliminary Report of Patentability for PCT Patent Application PCT/US2013/064146, dated Sep. 25, 2014.
PCT International Search Report and Written Opinion dated Jan. 9, 2014 for PCT Patent Application No. PCT/US2013/064146.
PCT International Preliminary Report on Patentability dated Feb. 1, 2013 for PCT Application No. PCT/US12/24798.
PCT International Search Report and Written Opinion dated Jun. 20, 2012 for PCT Application No. PCT/US12/24798.
PCT International Preliminary Report on Patentability dated Jan. 16, 2014 in related PCT Patent Application No. PCT/US12/66862.
PCT International Search Report and Written Opinion dated Feb. 12, 2013 for PCT Application No. PCT/US12/66862.
PCT International Search Report and Written Opinion dated Nov. 13, 2013 for PCT Patent Application No. PCT/US2013/054319.
PCT International Search Report and Written Opinion dated Nov. 19, 2013 for PCT Patent Application No. PCT/US2013/055003.
PCT International Search Report and Written Opinion dated Nov. 6, 2013 for PCT Patent Application No. PCT/US2013/054320.
PCT International Search Report and Written Opinion dated Oct. 22, 2013 for PCT Application No. PCT/US2013/054322.
PCT International Search Report and Written Opinion for PCT Application No. PCT/US2013/054325, dated Oct. 28, 2013.
PCT International Search Report and Written Opinion for related PCT Application No. PCT/US2016/050382, dated Nov. 14, 2016.
Rabbany et al., "Continuous Delivery of Stromal Cell-Derived Factor-1 From Alginate Scaffolds Accelerates Wound Healing", Cell Transplantation (2010), 19:399-408.
Tao et al., "Implantation of amniotic membrane to reduce postlaminectomy epidural adhesions," Eur. Spine. J., 18:1202-1212, (2009).
Unpublished U.S. Appl. No. 13/719,148, filed Feb. 13, 2012.
Unpublished U.S. Appl. No. 13/744,331, filed Jan. 17, 2013.
Unpublished U.S. Appl. No. 13/745,642, filed Jan. 18, 2013.
Unpublished U.S. Appl. No. 13/983,301, filed Aug. 1, 2013.
Zaja-Milatovic et al., "CXC Chemokines and Their Receptors: A case for a significant Biological Role in Cutaneous Wound Healing," Histol. Histopathol., 23(11):1399-1407, (2008).
Office Action for European Application No. 16770822.1 dated Mar. 28, 2019, 4 pages.
Annual Report of Cosmetology, 14:22-26 (2006). [in Japanese].
Office Action for Japanese Application No. 2018-511469 dated Apr. 20, 2021, 5 pages.

NON-SURGICAL, LOCALIZED DELIVERY OF COMPOSITIONS FOR PLACENTAL GROWTH FACTORS

CROSS-REFERENCE TO RELATED APPLICATIONS

This application is a continuation of U.S. application Ser. No. 15/797,335, filed Oct. 30, 2017, which is a continuation of U.S. application Ser. No. 14/845,199, filed Sep. 3, 2015, now U.S. Pat. No. 9,827,293, issued Nov. 28, 2017, which is a continuation-in-part of U.S. application Ser. No. 14/157,444, filed Jan. 16, 2014, now U.S. Pat. No. 9,655,948, issued May 23, 2017, which claims the benefit of U.S. Provisional Application Ser. No. 61/956,185, which was converted from U.S. application Ser. No. 13/744,331, filed Jan. 17, 2013; all of which are incorporated hereby by reference in their entirety.

BACKGROUND OF THE INVENTION

Field of the Invention

This invention is directed, in part, to compositions comprising placental growth factors and methods for non-surgical, localized delivery thereof. In one embodiment, the composition is delivered to a diseased or injured organ and/or body part and is co-delivered with an agent which allows for localized retention of the composition at the site of delivery.

State of the Art

Heretofore, modified placental tissue has been used to treat a diseased or injured internal organ or body part. However, such use has been limited by the amount of tissue available and the size of the organ. As a general rule, the minimum amount of modified placental tissue to elicit the desired result has been used. For example, in one embodiment, the placental tissue is used as a barrier layer between organs so as to prevent adhesion formation. See, for example, U.S. Patent Application Publication No. 2010/0104539.

The in vivo placement of a modified placental tissue also requires an invasive process whereby the placement requires an incision which typically accompanies surgery. However, injectable solutions containing a suspension of placental tissue recently have been used to provide for non-invasive delivery of the placental tissue. While this approach allows for direct delivery of the placental tissue to the in vivo delivery site, the size and amount of the placental tissue so delivered is limited by the width of the injection needle and the volume delivered.

Therefore the use of micronized placental tissue particles in an injectable form has provided significant benefits to disease or injured tissue. However, notwithstanding their commercial success, the retention time of such compositions in vivo is limited by virtue of their very large surface area arising from such micronized particles. The delivery or placement of compositions having less surface area than micronized particles, but more surface area than the placental tissue grafts from which they are formed, would provide for a more sustained benefit to the patient.

SUMMARY OF THE INVENTION

This invention is based, in part, on the discovery that a bioerodible or biodegradable mass formed from placental tissue allows for extended release of growth factors from the mass over a prolonged period of time.

This invention is also based on the discovery that localized delivery of the composition can be achieved by co-delivery in the solution or suspension of an agent which allows for localized retention of the solution or suspension at the site of delivery. Such agents include thixotropic agents, phase changing agents, and the like. When co-delivered, these agents form a viscous or gel-like bioerodible or biodegradable mass in vivo which limits transport away from the site of delivery and allows for the diffusion of the growth factors from the mass formed over a period of time.

Accordingly, in one aspect of this invention there is provided a composition comprising a defined surface area formed from micronized placental tissue, a sufficient amount of placental growth factor to treat a diseased or injured organ and a body part wherein said composition forms a localized mass when applied to or proximate to said diseased or injured organ or body part In another aspect of this invention, the composition contains modified placental tissue particles as defined herein. In another embodiment, the composition is free of modified placental tissue particles.

In another aspect, there is provided a method for preparing a composition for localized delivery of placental growth factors, which method comprises forming a porous bioerodible or biodegradable mass formed from micronized placental tissue. In another embodiment, the porous mass can be formed in situ by combining an aqueous suspension of placental tissue particles or an aqueous solution of placental growth factors with a sufficient amount of an agent which allows for localized retention of the solution or suspension at the site of delivery. Such agents include thixotropic agents, phase changing agents, and the like.

The biocompatible thixotropic agent is selected, by way of example only, from hyaluronic acid, collagen, thrombin gels, fibrin gels and fibrin glues. In another embodiment, the phase changing agent is a gel forming agent, such as a Pluronic® (e.g., a copolymer of oxyethylene and oxypropylene). Preferably, any polymer used as a thixotropic agent or a phase changing agent is bioerodible. In yet another embodiment, the body part is selected from the group consisting of skin, mucosal membrane, gum adjacent to teeth, bone, cartilage, tendon, retina, peripheral nerve, peripheral nerve sheath, small intestine, large intestine, stomach, skeletal muscle, heart, liver, lung, and kidney.

A thixotropic composition is one where in the absence of shear, the composition has infinite viscosity (it does not move) and in the presence of shear, the composition's viscosity is greatly reduced so as to be deliverable under shear. An example of a thixotropic composition is toothpaste. A phase-changing composition is an aqueous composition which undergoes a change from a liquid to a gel or solid mass based on a suitable trigger such as an increase in temperature, light activation, electromagnetic stimulation, the addition of a phase-changing co-factor (e.g., alginates plus calcium). Such compositions are well known in the art. These compositions are preferably deliverable under injection but also can be delivered topically as necessary. If the viscosity of the composition does not permit conventional injection, high pressure syringes can be used and are well known in the art. Non-limiting examples of such high pressure syringes include those described in U.S. Pat. No. 6,503,244 (incorporated herein by reference in its entirety) and the like.

In one aspect of this invention there are provided, compositions comprising a sufficient amount of placental growth factors to treat a diseased or injured organ and a body part wherein said composition is in the form of a localized bioerodible mass when applied to or proximate to said diseased or injured organ or body part, wherein said composition further comprises micronized placental tissue particles capable of being filtered through a sieve having a pore size from about 500 µm to about 10 µm.

In one aspect of this invention there are provided, methods for preparing a composition for localized delivery of placental growth factors, comprising combining an aqueous suspension of micronized placental tissue particles, the micronized placental tissue particles are capable of being filtered through a sieve having a pore size from about 500 µm to about 10 µm, an aqueous solution of placental growth factors, and a sufficient amount of a localization agent, whereby the composition is locally retained at the site of delivery upon administration.

In some embodiments, the composition further comprises a localization agent, for example, a thixotropic agent, or a phase changing agent. In some embodiments, the thixotropic agent is selected from the group consisting of hyaluronic acid, collagen, thrombin gels, fibrin gels and fibrin glues. In other embodiments, the phase changing agent is selected from the group consisting of a gel forming agent, for example, a copolymer or tripolymer of oxyethylene and oxypropylene units. In yet other embodiments, the localization agent is selected from the group consisting of a hydrogel, a polymer, and a collagen gel.

In some embodiments, the micronized placental tissue particles capable of being filtered through a sieve having a pore size from about 300 µm to about 10 µm, or from about 250 µm to about 25 µm.

DETAILED DESCRIPTION OF THE INVENTION

Before this invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

This invention is predicated in part on the discovery that the localized delivery of growth factors can be achieved either using a solution of such growth factors or a suspension of a sufficient amount of modified placental tissue combination with an agent that imparts a sufficient level of solidification in vivo so as to provide for a depot of growth factors to treat a diseased or injured body part.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" or "patient" as used herein refers to any vertebrate organism including, but not limited to, mammalian subjects such as humans, farm animals, domesticated pets and the like.

The term "amnion" as used herein includes amniotic membrane where the intermediate tissue layer is intact or has been substantially removed.

The term "exterior surface" refers to either or both surfaces of the modified placental tissue which will contact the organ of the patient to which tissue is applied.

The term "organ" as used herein is used to have an ordinary meaning in the art, and refers to organs constituting animal viscera in general.

The term "diseased" as used herein refers to an organ and/or body part that is characterized as being in a disease state, or susceptible to being in a disease state, wherein the disease is amenable to treatment with placental growth factors.

The term "injured" as used herein is used to have an ordinary meaning in the art, and includes any and all types of damage to an organ and/or body part, wherein the injury is amenable to treatment with placental growth factors.

The term "biocompatible" as used herein refers to a material that is suitable for implantation or injection into a subject. In various aspects, a biocompatible material does not cause toxic or injurious effects once implanted in the subject.

The term "modified placental tissue" refers to any and all components of placental tissue including whole placental tissue that has been modified by cleaning, disinfecting, and/or segmenting the tissue as well as to separated components of placental tissue such as amnion, chorion, the umbilical cord, and the like. Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "modified placental tissue particles" refers to modified placental tissue particles which have been made into particles small enough to form a suspension suitable for injection through a syringe. Such particles are preferably no more than about 300 microns in size, preferably less than about 250 microns, less than about 200 microns, less than about 150 microns, less than about 100 microns, or less than about 50 microns.

The term "placental growth factors" refers to that array of growth factors obtainable from modified placental tissue. The manner of obtaining such growth factors is not critical to the invention and include, by way of example only, aqueous extraction from the placenta, culturing of placental cells expressing such growth factors, and the like. The concentration of extracted growth factors can be increased by reducing the volume of water, saline, or buffer used to extract the growth factors, by addition of growth factors produced from placental cell cultures, and the like.

The term "sufficient amount" or "therapeutic amount" refers to an amount of placental growth factors that is sufficient to treat an injured or diseased organ or body part. The "sufficient amount" will vary depending on a variety of factors, such as but not limited to, the type and/or amount of placental tissue used, the type and/or size of the intended organ and/or body part to be treated, the severity of the disease or injury to the organ and/or body part to be treated and the administration route. The determination of a "sufficient amount" can be made by one of ordinary skill in the art based on the disclosure provided herein.

The term "proximate to" as used herein means adjacent to, or on a body part such that the placental growth factors exert the desired effect. In general, "proximate to" means a distance that is generally within the skill of the art but preferably is within about 3 cm, about 2 cm, about 1 cm of, or on or in the organ or body part.

As used herein, the term "bioerodible," which is used herein interchangeably with the term "biodegradable," refers to a biocompatible material that gradually decomposes, dissolves, hydrolyzes and/or erodes in situ, or that is susceptible to degradation into smaller components or molecules in a living organism over a prolonged period of time, for example, over days or months, such that the material is harmless to the living organism under normal living conditions. Generally, the "bioerodible" polymers herein are polymers that are hydrolyzable, and bioerode in situ primarily through hydrolysis. Preferably, the smaller components or molecules are biocompatible to a patient.

As one of ordinary skill in the art would understand, the degradation of the material results in a continuous release of a therapeutic amount of placental growth factors incorporated in the material over a prolonged period of time, such as about 3 days, about 5 days, about 10 days, about 15 days, about 20 days, about 25 days, about 30 days, about 2 months, about 3 months, about 4 months, about 5 months, or about 6 months. A desired release rate can be determined and/or achieved by adjusting the initial concentration of the growth factors incorporated in the bioerodible or biodegradable mass and the degradation rate of the mass.

A bioerodible or biodegradable mass has the benefit of localized retention at or proximate to the site of injection. In addition, placement of the bioerodible or biodegradable mass is configured to retain a substantial portion of the surface area found in the micronized placenta tissue components which form the mass. For example, the mass can be configured into a honeycomb shape whereby the pores provide for significant surface area retention. A mold containing a plurality of spikes, teeth, prongs, or the like in both the male and female mold halves will result in a porous bioerodible or biodegradable mass having significant amounts of surface area. Additional surface area can be created by laser drilling into the mass. Other means to form a porous mass are well known in the art. As discussed above, a bioerodible or biodegradable mass retains a substantial portion of its surface area. For example, a bioerodible or biodegradable mass may retain about 5%, about 10%, about 20%, about 30%, about 40%, or about 50% of its surface area for a period of time such as, for example, about 3 days, about 5 days, about 10 days, about 15 days, about 20 days, about 25 days, about 30 days, about 2 months, about 3 months, about 4 months, about 5 months, or about 6 months. In all cases such is significantly greater than a placental tissue graft. Of course the degradation rate will depend upon the amount of surface area exposed in vivo, whereby the greater the exposed surface area the faster the rate of degradation.

The period for sustained release of growth factors from the bioerodible or biodegradable mass relates to the surface area exposed to physiological fluid when said mass is injected or implanted in vivo. Based on the information provided herein, the skilled artisan can routinely assess the duration of sustained release based directly, at least in part, on the size of the mass and surface area of the mass. Using such parameters, the skilled artisan can form a suitable mass with a predetermined period of sustained release by simple correlations.

Titles or subtitles may be used in the specification for the convenience of a reader, which are not intended to influence the scope of the present invention. Additionally, some terms used in this specification are more specifically defined below.

In one embodiment, placental tissue may be modified as described in U.S. Provisional Application Ser. No. 61/683,698, including cleaning, separation of the amnion and chorion, removal or maintenance of the epithelial cell layer, decontamination, and dehydration. Dehydration may be accomplished using the drying apparatus as described in U.S. Provisional Application Ser. No. 61/683,698. Both of which applications are incorporated herein by reference in their entireties. Each aspect of that process produces modified placental tissue for the purposes of this invention whether used alone or in combination. However, it is preferred that the modification of placental tissue includes at least the steps of cleaning and decontamination. As such, modified placental tissue preferably comprises placental tissue which has been cleaned and decontaminated and also includes placental tissue which has undergone one or more of separation of the amnion and chorion, removal of the epithelial cell layer, and dehydration.

In some embodiments of the present technology, the modified placental tissue is selected from amnion, chorion, or both amnion and chorion. In exemplary embodiments, modified placental tissue does not include the umbilical cord.

Modified placental tissue can also be formed into layers which may be dried separately and laminated together or dried together to form multi-layer laminates.

Described herein are compositions composed of micronized placental components and pharmaceutical compositions thereof. In one aspect, the composition includes (a) micronized amnion, chorion, intermediate tissue layer, or any combination thereof and (b) a pharmaceutically acceptable carrier. In one aspect, the composition includes micronized amnion and intermediate tissue layer. In another aspect, the composition includes micronized amnion and chorion. Micronized placental tissue may be sandwiched between one or more layers of a multilayer laminate, or on top of a laminate. Micronized placental tissue may also be added to a single layer of modified placental tissue. See, for example, U.S. Provisional Application Ser. No. 61/683,700, which is incorporated herein by reference in its entirety.

Once the amnion, chorion, and/or intermediate tissue layer have been dehydrated individually or in the form of a tissue graft, the dehydrated tissue(s) is micronized. The micronized compositions can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 µm, less than 400 µm, less than 300 µm, or from 25 µm to 300 µm, from 25 µm to 200 µm, or from 25 µm to 150 µm. In certain aspects, particles having a larger diameter (e.g. 150 µm to 350 µm) are desirable.

Any method known by one of skill in the art may be used to separate particles by size including by, for example, centrifugation, sedimentation, and sieve techniques. In one embodiment, sieves are used to separate particles by size. The sieve size (i.e., the sieve pore opening) is about 500 µm to about 10 μm, about 400 μm to about 20 μm, about 350 μm to about 25 μm, about 300 μm to about 35 μm, about 300 μm to about 45 μm, about 250 μm to about 50 μm, about 210 μm to about 60 μm, about 175 μm to about 75 μm, about 150 μm to about 80 μm, about 125 μm to about 100 μm, or any range therein. In some embodiments the sieve size (e.g., opening) is about 500 μm, about 400 μm, about 350 μm, about 300 μm, about 250 μm, about 210 μm, about 175 μm, about 150 μm, about 125 μm, about 100 μm, about 80 μm, about 75 μm, about 60 μm, about 50 μm, about 45 μm, about 35 μm, about 25 μm, about 20 μm, about 10 μm.

One of skill in the art will appreciate that when particles are separated using a sieve, a dimension of at least a portion of the particles may be larger than the opening of the sieve used. Said another way, when the shape of a particle resembles that more of a rod, the longer axis may be about 25% longer than the shorter axis and therefore a particle having a shorter axis of under 75 μm but with a longer axis of about 100 μm may still be collected using a 75 μm sieve. In some embodiments, the longer axis of a micronized placental particle may be about 30% longer than the shorter axis, about 25% longer than the shorter axis, about 20% longer than the shorter axis, about 15% longer than the shorter axis, about 10% longer than the shorter axis, about 5% longer than the shorter axis, or about 1% longer than the shorter axis.

In one aspect, micronization is performed by mechanical grinding or shredding. In another aspect, micronization is performed cryogenic grinding. In this aspect, the grinding jar containing the tissue is continually cooled with liquid nitrogen from the integrated cooling system before and during the grinding process. Thus the sample is embrittled and volatile components are preserved. Moreover, the denaturing of proteins in the amnion, intermediate tissue layer, and/or chorion is minimized or prevented. In one aspect, the CryoMill manufactured by Retsch can be used in this aspect.

The selection of components used to make the micronized components described herein can vary depending upon the end-use of the composition. For example, amnion, chorion, intermediate tissue layer, or any combination thereof as individual components can be admixed with one another and subsequently micronized. In another aspect, one or more tissue grafts composed of one or more amnion, chorion, intermediate tissue layers, or any combination thereof (i.e., laminates) can be micronized. In a further aspect, one or more tissue grafts composed of one or more amnion, chorion, intermediate tissue layers, or any combination can be admixed with amnion, chorion, intermediate tissue layer, or any combination thereof as individual components and subsequently micronized.

The amount of different components used to make the micronized compositions described herein can vary depending upon the application of the micronized composition. In one aspect, when the micronized composition is composed of amnion (with or without the intermediate tissue layer) and intermediate tissue layer, the weight ratio of amnion to intermediate tissue layer is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1. In another aspect, when the micronized composition is composed of amnion (with or without the intermediate tissue layer) and chorion, the weight ratio of chorion to amnion is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1.

In addition to amnion, the intermediate tissue layer, and chorion, additional components can be added to the composition prior to and/or after micronization. In one aspect, a filler can be added. Examples of fillers include, but are not limited to, allograft pericardium, allograft acellular dermis, Wharton's jelly separated from vascular structures (i.e., umbilical vein and artery) and surrounding membrane, purified xenograft Type-1 collagen, biocellulose polymers or copolymers, biocompatible synthetic polymer or copolymer films, purified small intestinal submucosa, bladder acellular matrix, cadaveric fascia, or any combination thereof.

In another aspect, a bioactive agent can be added to the composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the micronized composition with bioactive agent to the region of interest, the bioactive agent is delivered to the region over time. Thus, the micronized particles described herein are useful as delivery devices of bioactive agents and other pharmaceutical agents when administered to a subject. Release profiles can be modified based on, among other things, the selection of the components used to make the micronized compositions as well as the size of the particles.

In a further aspect, the amnion can be cross-linked with the intermediate tissue layer, chorion, or a second amnion tissue. For example, a cross-linking agent can be added to the composition (e.g., amnion, chorion, intermediate tissue layer, or any combination thereof as individual components and/or as tissue grafts) prior to and/or after micronization. In general, the cross-linking agent is nontoxic and non-immunogenic. When the amnion, intermediate tissue layer, and/or chorion (or a tissue graft thereof) are treated with the cross-linking agent, the cross-linking agent can be the same or different. In one aspect, the amnion, intermediate tissue layer, and chorion can be treated separately with a cross-linking agent or, in the alternative, the amnion, intermediate tissue layer, and chorion can be treated together with the same cross-linking agent. In certain aspects, the amnion, intermediate tissue layer, and chorion can be treated with two or more different cross-linking agents. The conditions for treating the amnion, intermediate tissue layer, and chorion can vary. In other aspects, the amnion, intermediate tissue layer, and/or chorion can be micronized, and the micronized composition can subsequently be treated with a cross-linking agent. In one aspect, the concentration of the cross-linking agent is from 0.1 M to 5 M, 0.1 M to 4 M, 0.1 M to 3 M, 0.1 M to 2 M, or 0.1 M to 1 M.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the amnion, intermediate tissue layer, and chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerone, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof.

In certain aspects, the micronized composition can be used to form a three-dimensional construct. For example, the micronized particles can be treated with a cross-linking agent described above then placed in a mold having specific dimensions. Alternatively, the micronized particles can be placed into the mold and subsequently treated with the cross-linking agent. In one aspect, the cross-linked particles can be manually formed into any desired shape. In other aspects, one or more adhesives can be admixed with an adhesive prior to being introduced into the mold. Examples of such adhesives include, but are not limited to, fibrin sealants, cyanoacrylates, gelatin and thrombin products, polyethylene glycol polymer, albumin, and glutaraldehyde products. Not wishing to be bound by theory, the three-dimensional construct composed of smaller micronized particles will produce a denser product capable of bearing mechanical loads. Alternatively, larger micronized particles will produce constructs that are less dense and possess compressive properties. This feature can be useful in non-load void filling, especially where it is desirable to have a product that will conform to irregular shapes. The three-dimensional constructs can include one or more bioactive agents described herein.

A bioerodible or biodegradable mass formed by the molds described above can have an added benefit of an increased surface area. Additionally, a mold can create a number of indentations, undulations, or the like on the surface and/or within the mass such that the surface area is further increased. Decreasing the surface area of the bioerodible or biodegradable mass allows for a slower rate of degradation such that the mass may take, for example, two, three, four, five, or more times as long to decompose, dissolve, hydrolyze and/or erode. A bioerodible or biodegradable mass that remains localized and degrades slowly would be particularly beneficial for treating a wound or diseased or injured tissue that requires a prolonged treatment regimen.

In other aspects, the micronized compositions described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. Additionally, the pharmaceutical compositions can include carriers, thickeners, diluents, preservatives, surface active agents and the like in addition to the compounds described herein.

The pharmaceutical compositions can be prepared using techniques known in the art. In one aspect, the composition is prepared by admixing a micronized composition described herein with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound.

It will be appreciated that the actual preferred amounts of micronized composition in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

The pharmaceutical compositions described herein can be administered in a number of ways depending on whether local or systemic treatment is desired, and on the area to be treated. In one aspect, administration can be by injection, where the micronized composition is formulated into a liquid or gel. In other aspects, the micronized composition can be formulated to be applied internally to a subject. In other aspects, the micronized composition can be applied topically (including ophthalmically, vaginally, rectally, intranasally, orally, or directly to the skin).

In one aspect, the micronized compositions can be formulated as a topical composition applied directly to the skin. Formulations for topical administration can include, emulsions, creams, aqueous solutions, oils, ointments, pastes, gels, lotions, milks, foams, suspensions and powders. In one aspect, the topical composition can include one or more surfactants and/or emulsifiers.

In some embodiments, localization agents, such as thixotropic agents, phase changing agents, and the like, may include but not limited to, hydrogel, bioerodible, biocompatible polymer, and collagen gels. The presence of one or more localization agents in the compositions of this invention allows the compositions to have certain viscosity such that the compositions are locally retained for a period of time upon administration or injection. It is within the purview of one of ordinary skill in the art to determine the suitable viscosity of the compositions. In some aspects, the compositions have a viscosity between about 5 cP to about $1 \times 10^8$ cP, or about 5 cP to about $1 \times 10^6$ cP, or about 5 cP to about $1 \times 10^5$ cP, or about 5 cP to about $1 \times 10^4$ cP, or about 5 cP to about $1 \times 10^3$ cP, or about 6 cP to about 9500 cP at 25° C.

The hydrogels useful in the compositions of this invention can be chemically and/or physically cross-linked hydrogels. In situ chemical cross-linking is obtained, e.g., via photo-initiated, redox-initiated or Michael-type addition polymerization that preferably involve covalent bond formation.

Physically cross-linked hydrogels self-assemble under external stimuli and do not rely on covalent bond formation. Temperature, pH, ion concentration, and hydrophobic interactions are certain of the external stimuli useful for such self-assembly and for the immobilization of such hydrogels.

Exemplary polymers suitable for the use in the composition of the present invention include polylactides, polyglycolides, poly(caprolactone), polyanhydrides, polyamines, polyesteramides, polyorthoesters, polydioxanones, polyacetals, polyketals, polycarbonates, polyphosphoesters, polyorthocarbonates, polyphosphazenes, succinates, poly(malic acid), poly(amino acids), polyvinylpyrrolidone, polyethylene glycol, polyhydroxycellulose, polyphosphoesters, polysaccharides, chitin, chitosan, hyaluronic acid, and copolymers, terpolymers and mixtures thereof.

Collagens useful in the present invention include Type I, Type III or Type I+III collagens, for example, alkaline treatment of insoluble collagen extracted from various animals, or by treating with enzyme such as pepsin, trypsin, chymotrypsin, papin or pronase. There are no particular restrictions on the origin of the collagen, and typically collagen can be used that is obtained from the skin, bone, cartilage, tendon or organs, etc. of birds or mammals. Since collagen allows the obtaining of a suitable consistency without heating, preparation can be made easily in the case of gelation. In addition, collagen has a high molecular weight, it more closely resembles living body tissue, has considerable physiological activity, and therefore promotes healing in the case of using on a wound, resulting in a further therapeutic effect in combination with the modified placental tissue. Collagen can be flexible after curing and requires only a short time for crosslinking, in other words, requires only a short time for gelation. Collagen solution can also be made by dissolving in a non-toxic solvent respect to the living body, examples of which include water, physiological saline, a buffer such as borate buffer, or an aqueous solution containing a salt such as sodium chloride, sodium bromide and potassium bromide, or protein, sugar or lipid, etc.

The collagen can also form a gel even in the presence of moisture such as that in blood or humor, and can demonstrate a high degree of adhesiveness with respect to living body tissue. Collagen solutions used in the present invention can be made at various concentrations, neutralized and prepared for injection. In various aspects, collagen at 0.2 mg/mL, 0.5 mg/mL, 0.75 mg/mL, 1 mg/mL, 2 mg/mL, 3 mg/mL, 4 mg/mL, 5 mg/mL, 6 mg/mL, 7 mg/mL, 8 mg/mL, 10 mg/mL, 20 mg/mL, 30 mg/mL, 40 mg/mL and 50 mg/mL in solution can be used for injection. Upon injection into an organ, chilled collagen gels can thermogel as they reach body temperature or about 37° C.

Other embodiments and uses of the invention will be apparent to those skilled in the art from consideration of the specification and practice of the invention disclosed herein. The specification and examples that follow should be considered exemplary only.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1—Extraction of Placental Growth Factors

A desired amount of modified placental tissue, which has been previously cleaned, is extracted in 1M NaCl solution at 4° C. at a solution:modified placental tissue ratio of 10:1 (w/w) for 24 hours. Optionally, the extraction is carried out using a rocker platform under agitation. Following extraction, the supernatant is separated from residues by centrifugation. The collected supernatant is then dialyzed against water, and subsequently, the solution containing the placental growth factors is lyophilized. Upon administration, the lyophilized placental growth factors may be reconstituted in water for injection at a predetermined concentration.

Example 2—Preparation of an Immobilized Composition

Five mL of EpiFix® injectable solution containing a suspension of modified placental tissue particles (available from MiMedx Group Inc., Kennesaw, Ga., USA) is cooled to 5° C. To this solution is added approximately 20% w/w of poloxomer PF-127 which is a commercially available polyoxyethylene-polyoxypropylene triblock copolymer of general formula E106 P70 E106, with an average molar mass of 13,000 (25,26). The resulting composition retains its liquid properties at 5° C. but will gelatinate at approximately 20° C.

The cold solution is loaded into a 10 mL syringe and then immediately used to inject the solution into a knee joint of a patient exhibiting a partially torn cartilage. Upon injection, the body temperature causes a phase-transfer to a bioerodable gel which will elute the growth factors during erosion.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A composition comprising a sufficient amount of placental growth factors to treat a diseased or injured organ or body part wherein said composition is in the form of a localized mass when applied to or proximate to said diseased or injured organ or body part; wherein said composition is free of modified placental tissue particles; wherein said growth factors are extracted from modified placental tissue; and wherein said modified placental tissue comprises chorion.

2. The composition of claim 1, further comprising a localization agent.

3. The composition of claim 2, wherein the localization agent is a thixotropic agent, or a phase changing agent.

4. The composition of claim 3, wherein the thixotropic agent is selected from the group consisting of hyaluronic acid, collagen, thrombin gels, fibrin gels and fibrin glues.

5. The composition of claim 3, wherein the phase changing agent is a gel forming agent.

6. The composition of claim 5, wherein the gel forming agent is a copolymer or tripolymer of oxyethylene and oxypropylene units.

7. The composition of claim 2, wherein the localization agent is selected from the group consisting of a hydrogel, a polymer, and a collagen gel.

8. The composition of claim 1, wherein the composition forms a localized bioerodible mass when applied to or proximate to said diseased or injured organ or body part.

9. The composition of claim 1, wherein said modified placental tissue further comprises amnion.

10. A method for preparing a composition for localized delivery of placental growth factors, comprising combining an aqueous solution of placental growth factors with a sufficient amount of a localization agent, whereby the composition is locally retained at the site of delivery upon administration; wherein said composition is free of modified placental tissue particles; wherein said growth factors are extracted from modified placental tissue; and wherein said modified placental tissue comprises chorion.

\* \* \* \* \*